United States Patent
Walker et al.

(10) Patent No.: US 9,127,281 B2
(45) Date of Patent: Sep. 8, 2015

(54) SIRNA MOLECULES FOR THE TREATMENT OF BLOOD VESSELS

(75) Inventors: Tobias Walker, Tübingen (DE); Hans-Peter Wendel, Balingen (DE)

(73) Assignee: Eberhard-Karls-Universität Tübingen Universitätsklinikum, Tübingen (DE)

( * ) Notice: Subject to any disclaimer, the term of this patent is extended or adjusted under 35 U.S.C. 154(b) by 1334 days.

(21) Appl. No.: 11/814,213

(22) PCT Filed: Jan. 19, 2006

(86) PCT No.: PCT/EP2006/000447
§ 371 (c)(1),
(2), (4) Date: Feb. 13, 2008

(87) PCT Pub. No.: WO2006/077112
PCT Pub. Date: Jul. 27, 2006

(65) Prior Publication Data
US 2008/0260854 A1    Oct. 23, 2008

(30) Foreign Application Priority Data
Jan. 19, 2005    (DE) .......................... 10 2005 003 788

(51) Int. Cl.
| C07H 21/04 | (2006.01) |
| C12N 15/113 | (2010.01) |
| A61L 27/34 | (2006.01) |
| A61L 31/10 | (2006.01) |
| A61K 48/00 | (2006.01) |

(52) U.S. Cl.
CPC ............. C12N 15/1138 (2013.01); A61L 27/34 (2013.01); A61L 31/10 (2013.01); C12N 15/1135 (2013.01); *A61K 48/00* (2013.01); *C12N 2310/14* (2013.01)

(58) Field of Classification Search
None
See application file for complete search history.

(56) References Cited

U.S. PATENT DOCUMENTS

| 6,436,644 B1 * | 8/2002 | Grimm et al. ...................... 435/6 |
| 7,638,622 B2 * | 12/2009 | Khvorova et al. ........... 536/24.5 |
| 2003/0157030 A1 * | 8/2003 | Davis et al. ...................... 424/46 |
| 2004/0220129 A1 | 11/2004 | Reich et al. |

FOREIGN PATENT DOCUMENTS

| EP | 03020437.4 | * 9/2003 |
| WO | WO 03/099298 | 12/2003 |
| WO | WO 03/104456 | 12/2003 |
| WO | WO 2004/030634 | 4/2004 |
| WO | WO 2004/045543 | 6/2004 |
| WO | WO 2004/065546 | 8/2004 |
| WO | WO2005/024033 | * 9/2004 ............. C13N 15/87 |

OTHER PUBLICATIONS

Opti-MEM Invitrogen [online]. [retrieved on Apr. 5, 2010]. Retrieved from the Internet: <http://www.invitrogen.com/site/us/en/home/Products-and-Services/Applications/Cell-Culture/Mammalian-Cell-Culture/Classical_Media/Opti-MEM.html>.*

Suda, et al. (2001) [Abstract] Phenotypic Characterization of Human Umbilical Vein Endothelial (ECV304) and Urinary Carcinoma (T24) Cells: Endothelial Versus Epithelial Features. In Vitro Cell Dev. Biol. Anim., v.38(4):185-6.*

Nishiwaki Y. et al., "Introduction of short interfering RNA to silence endogenous E-selectin in vascular endothelium leads to successful inhibition of leukocyte adhesion," *Biochemical and Biophysical Research Communications*310(4): 1062-1066, 2003.

Walker et al., "Suppression of ICAM-1 in human venous endothelial cells by small interfering RNAs," *European J. Of Cardio-thoracic Surgery*28(6): 816-820, 2005.

Bonatti et al., "Kardiovaskuläre Gentherapie—was kann der Chirurg derzeit davon erwarten?," *J. Kardiol*9:14-20, 2002.

Brummelkamp et al., "A system for stable expression of short interfering RNAs in mammalian cells," *Science*296: 550-553, 2002.

Chello et al.," Pressure distension stimulates the expression of endothelial adhesion molecules in the human saphenous vein graft," *Ann. Thorac. Surg.*76(2):453-458, 2003.

Chiu et al., "siRNA Function in RNAi: A chemical modification analysis," *RNA*9(9): 1034-1048, 2003.

DeMeester et al., "Attenuation of Rat Lung Isograft Reperfusion Injury with a Combination of Anti-ICAM-1 and Anti-$\beta eta_2$ Integrin Monoclonal Antibodies," *Transplantation*62(10): 1477-1485, 1996.

Egan et al., "Trigger for Intracellular Adhesion Molecule-1 Expression in Rat Lunds Transplanted from Non-Heart-Beating Donors," *Ann.Thorac. Surg.*77(3): 1048-1055, 2004.

Elbashir et al., "Duplexes of 21-nucleotide RNAs mediate RNA interference in cultured mammalian cells," *Nature*410(6836): 494-498, 2001.

Jaffe et al., "Culture of human endothelial cells derived from umbilical veins. Identification by morphologic and immunologic criteria," *J. Clin. Invst.*52(11): 27452756, 1973.

(Continued)

*Primary Examiner* — Kimberly Chong
(74) *Attorney, Agent, or Firm* — Klarquist Sparkman, LLP

(57) ABSTRACT

The present invention relates to a nucleic acid molecule, a genetic construct, siRNA molecules and a composition which comprises the nucleic acid molecule and/or the genetic construct and/or the siRNA molecules and can be used for inhibition of the expression of endothelial adhesion molecules. The invention also relates to a device, which is coated with the aforementioned molecules, the composition or the construct, or contains them. The present invention further relates to a corresponding use of the nucleic acid molecule, of the genetic construct or of the siRNA molecules and a method of inhibition of the expression of adhesion molecules and a method of vessel grafting, lung transplantation, treatment of lung transplants, and a method of treatment of the open heart within the scope of cardioplegia.

19 Claims, 6 Drawing Sheets

(56) References Cited

OTHER PUBLICATIONS

Kretschmer-Kazemi Far R. et al., "The activity of siRNA in mammalian cells is related to structural target accessibility: a comparison with antisense oligonucleotides," *Nucleic Acids Res.* 31(15), 4417-4424, 2003.

Lee et al., "Expression of small interfering RNAs targeted against HIV-1 *rev* transcripts in human cells," *Nat. Biotechnol.* 20:500-505, 2002.

Maeshima et al., "Inhibition of Mesangial Cell Proliferation by E2F Decoy Oligodeoxynucleotide in Vitro and in Vivo," *J. Clin. Invest.* 101(11):2589-2597, 1998.

Meyers et al., "Primary Graft Dysfunction and other Selected Complications of Lung Transplantation: A Single Center Experience of 983 Patients," *J. Thorac. Cardiovasc. Surg.* 129(6): 1421-1429, 2005.

Miyagishi et al., "Development and application of siRNA expression vector," *Nucleic Acids Res.* [Suppl]: 113-114, 2002.

Morrissey et al., "Potent and persistent in vivo anti-HBV activity of chemically modified siRNAs," *Nat. Biotechnol.* 123(8): 1002-1007, 2005.

Nachman, R. L. et al., "Endothelial cell culture: beginnings of modern vascular biology," *J. Clin. Invest.* 114(8): 1037-1040, 2004.

Nedbal et al., "Antisense-mediated inhibition of ICAM-1 expression: a therapeutic strategy against inflammation of human periodontal tissue," *Antisense & Nucleic Acid Drug Dev.* 12(2): 71-78, 2002.

Shreeniwas et al., "Adhesion Molecules (E-Selectin and ICAM-1) in Pulmonary Allograft Rejection," *Chest.* 110(5): 1143-1149, 1996.

Wadhwa et al., "Know-how of RNA interference and its applications in research and therapy," *Mutat. Res.* 567(1): 71-84, 2004.

\* cited by examiner

SIRNA MOLECULES FOR THE TREATMENT OF BLOOD VESSELS

CROSS REFERENCE TO RELATED APPLICATIONS

This application is the U.S. National Stage of copending International Application No. PCT/EP2006/000447, filed Jan. 19, 2006, which in turn claims the benefit of German Patent Application No. DE 10 2005 003 788.7 filed on Jan. 19, 2005. All of these applications are incorporated herein by reference in their entirety.

The present invention relates to a nucleic acid molecule, a genetic construct, siRNA molecules and a composition which comprises the nucleic acid molecule and/or the genetic construct and/or the siRNA molecules and can be used for inhibition of the expression of endothelial adhesion molecules, in particular on the pulmonary, cardiac and vascular flow path. The invention also relates to a device which is coated with or contains the aforementioned molecules, the composition or the construct. The present invention further relates to a corresponding use of the nucleic acid molecule, of the genetic construct or of the siRNA molecules and a method of inhibition of the expression of adhesion molecules, a method of vessel transplantation, lung transplantation or lung-transplant treatment, and a method for open-heart treatment within the scope of cardioplegia.

In Western industrialized countries, so-called coronary heart disease is among the commonest causes of death. This is taken to mean inadequate blood supply to the heart muscle caused by narrowing of the coronary vessels. This inadequate blood supply leads—mainly on exertion—to an imbalance of oxygen supply and demand. The principal cause of coronary heart disease is arteriosclerosis of the coronary arteries of the heart. Possible consequences are angina pectoris with resultant chest pains, and myocardial infarction.

The drugs currently used for treating coronary heart disease, so-called coronary therapeutic agents, include nitrates, also called nitro compounds, beta-blockers and calcium antagonists. These substances have the effect that the heart requires less oxygen to function, and so is under less strain. The oxygen deficiency of the heart caused by coronary heart disease is partially compensated.

However, a disadvantage of this drug treatment is that, especially when the disease is at an advanced stage, often it is no longer possible to achieve sufficient relief of the strain on the heart. Many common drugs for treating coronary heart disease also have undesirable side effects.

An invasive approach for the treatment of coronary heart disease is to perform an angioplasty. In this procedure, a balloon catheter is introduced into the narrowed coronary vessel and then inflated in an attempt to expand the vessel volume and to smooth the inside wall of the vessel. Angioplasty is usually combined with the insertion of a stent, to ensure permanent dilation of the blocked or narrowed vessel.

However, this technique presents a great many risks for the patient, due to the invasiveness of the procedure. Furthermore, this procedure is contraindicated if there is very pronounced sclerosis of the stenosis, disturbance of blood clotting or unfavourable anatomical location of the vessel. In addition, there may be postoperative bleeding, thrombosis, embolism, perforation, dissection etc. As this procedure cannot guarantee permanent protection against renewed obstruction of the vessel, in many cases it is necessary for angioplasty to be repeated. The patient is then exposed once again to the risks mentioned above. Once the disease has progressed, heart surgery is unavoidable.

Another therapeutic approach to the treatment of coronary heart disease comprises the transplantation of vessels, for example an autologous segment of the vena saphena, in the form of a bypass. This intervention aims to get round a stenosis or complete obstruction of one or more coronary arteries by inserting a transplant between the aorta and the coronary artery. This operation is now the standard method in invasive therapy of coronary heart disease. The operation is performed on about 1 million patients per year throughout the world, and about 80 000 in Germany alone.

The bypass transplants used are subject to a large number of intraoperative stress factors: mechanical damage, stretching, hypoxia, hypothermia, cytokine stimulation via the heart-lung machine, etc. In addition, after successful revascularization, the originally venous vessel is exposed to an arterial pressure, leading to severe loading of the vessel.

All these factors lead to fulminant endothelial activation, giving rise to increased transendothelial migration of leukocytes mediated by intercellular adhesion molecules, massively impairing the integrity of the endothelium and thus contributing substantially to early bypass stenosis; cf. Chello et al. (2003), Pressure distension stimulates the expression of endothelial adhesion molecules in the human saphenous vein graft, Ann. Thorac. Surg. 76(2), p. 453-458. Thus, the patency rate of bypass transplants after 10 years when using arterial vessels, for example arteria mammaria interna, is still 92%, whereas when venous vessels are used, for example the vena saphena, it is only 60%. So far, no precise data are available regarding early occlusion rates in the initial days and weeks.

The first gene-therapy techniques, which aim to prevent bypass stenosis, have already been described in the prior art. For example, Maeshima et al. (1998), Inhibition of Mesangial Cell Proliferation by E2F Decoy Oligodeoxynucleotide in vitro and in vivo, J. Clin. Invest., p. 2589-2597, describe a synthetic oligonucleotide that is able to bind to the E2F transcription factor. The authors showed that after transfection of the oligonucleotide into mesangial cells, expression of the E2F transcription factor and of the PCNA (proliferating cell nuclear antigen) protein is inhibited and therefore the proliferation of these cells is prevented. The company Corgentech Inc., San Francisco, USA, offers such an oligonucleotide under the designation "E2F decoy" as a therapeutic agent for the prevention of bypass stenosis; cf. www1.corgentech.com/cgt/edifoligide.

However, inhibition of the function of E2F is extremely critical within the scope of a therapeutic application. Thus, it is known that E2F is not only responsible for a pathological proliferation of endothelial cells. In fact, E2F is a central transcription factor, which activates a large number of genes that encode proteins regulating the cell cycle, for example dihydrofolate reductase, c-myc, DNA-polymerase, cdc2 and PCNA. Therefore insertion of an oligonucleotide that inhibits the E2F function also prevents essential repair mechanisms, e.g. connected with wound healing or natural regeneration of the vessels, from taking place. Patients who receive correspondingly transfected bypass transplants are therefore exposed to an increased risk of myocardial infarction or other heart diseases.

The currently known gene-therapy measures in connection with cardiovascular diseases are reviewed in Bonatti et al. (2002), Kardiovaskuläre Gentherapie—was kann der Chirurg derzeit davon erwarten? (Cardiovascular gene therapy—what can the surgeon expect from it at present?), J. Kardiol. 9, pages 14 to 20.

Furthermore, diseases of the respiratory tract, and especially of the lungs, pose a serious challenge to modern medicine and pharmaceutical research. For many patients so affected, a lung transplant represents the last possible treatment for obtaining an improvement of the quality of life. In the ideal situation, this can provide an increase in exercise tolerance, withdrawal from continuous oxygen therapy and therefore a marked improvement in the patient's circumstances. Viewed globally, the number of lung transplants carried out is continuously increasing.

Since 1998, the number of patients waiting for a lung transplant has increased by more than 250%, and the number of transplants carried out has only increased by 70%, according to official statistics from Euro Transplant, Leyden, Germany. In other words there is an increasing shortage of donor organs. This shortage arises partly because at present only organs are used from donors with an almost intact cardiovascular situation at the moment of organ removal, so-called beating-heart donors (BHD).

One possibility for overcoming the organ shortage is offered by the use of transplant organs from donors whose heart is no longer beating at the time of removal, so-called non-heart-beating donors (NHBD).

In both cases, between the moment of organ removal and reimplantation in the recipient, the organ is not supplied with blood—it is ischaemic. As described above for bypass transplants, this ischaemia induces considerable activation of the endothelium in the lung transplant as well, leading to expression of inflammatory adhesion molecules in the pulmonary microvascular flow path. Leukocytes bind to these inflammatory adhesion molecules.

There is then transendothelial migration of leukocytes from the endovascular lumen into the organ parenchyma and subsequent impairment of pulmonary membrane integrity. In 20 to 40% of cases this impairment is so pronounced that clinically relevant pulmonary oedema occurs. This is also called primary graft failure (PGF). PGF is associated with a marked increase in co-morbidity and therefore an impaired primary outcome of the transplant patients; cf. Meyers et al. (2005), Primary Graft Dysfunction and other Selected Complications of Lung Transplantation: A Single Center Experience of 983 Patients, J. Thorac. Cardiovasc. Surg. 129 (6), p. 1421-1429.

It is known from animal experiments that in organs of NHBDs the microvascular endothelial cell activation is even more fulminant and therefore the outcome of the transplant patients is much poorer, so that these organs have not previously been recruited; cf. Egan et al. (2004), Trigger for Intracellular Adhesion Molecule-1 Expression in Rat Lungs Transplanted from Non-Heart-Beating Donors, Ann. Thorac. Surg. 77 (3), p. 1048-1055. If the outcome of NHBD-transplanted organs could be matched to the outcome of BHD-transplanted organs by means of drug therapy, the number of patients waiting for a lung transplant could be reduced considerably, as more organs would be available for transplanting.

To date, there is no specific way of exerting a specific, targeted influence on microvascular endothelial cell activation in lung transplants, to reduce the incidence of PGF. DeMeester et al. (1996), Attenuation of Rat Lung Isograft Reperfusion Injury with a Combination of Anti-ICAM1 and Anti-beta2 Integrin Monoclonal Antibodies, Transplantation 62 (10), p. 1477-1485, describe the blocking of inflammatory adhesion molecules in animal experiments with antibodies. Although a marked improvement in transplant outcome was achieved with this procedure, this therapy has not been widely adopted owing to considerable antibody-associated side effects.

Within the scope of cardioplegia, in open-heart operations a reversible cardiac arrest is induced artificially. This cardiac arrest can be brought about for example by so-called cardioplegic solutions, which are ice-cold and pH-neutral, and contain potassium and magnesium. During cardiac arrest there is accumulation of toxic metabolic products, carbon dioxide and lactic acid in the heart and therefore acidosis. These factors, combined with ischaemia, can permanently damage the myocardial cells.

The object of the present invention is therefore to provide therapeutically effective substances, with which the problems described above in connection with early bypass stenosis of venous transplants, primary failure of lung transplants and cardioplegia can be avoided.

In particular, substances are to be provided which can be manufactured easily and can be used, for example during a heart operation, bypass operation or lung transplantation, so that stenosis or graft failure is prevented.

This object is accomplished according to the invention by the provision of a nucleic acid molecule, which inhibits the expression of adhesion molecules and comprises at least one of the nucleotide sequences SEQ ID No. 1-44 in the accompanying sequence listing.

Surprisingly, by means of such a nucleic acid molecule which can for example be transfected into biological cells in the form of a so-called siRNA (small interfering RNA) molecule, the inventors succeeded in preventing the development of stenosis or impairment of pulmonary membrane integrity or of the heart during cardioplegia. These siRNA molecules comprise double-stranded structures of ribonucleic acid, which are able to initiate a posttranscriptional process, which is designated RNA interference (RNAi) and leads to inactivation of the expression of certain genes, so-called gene silencing. When inserted in a biological cell, the siRNA molecules are recruited to a so-called ribonuclease complex, called the RNA-induced silencing complex (RISC). This complex is able, via the siRNA molecule, to bind to substantially complementary structures, such as the mRNA of a transcribed gene, and degrade them by endonuclease activity. This leads ultimately to inhibition of expression of the corresponding gene that encodes the mRNA that is complementary to the siRNA molecule and is degraded.

Before now, it was by no means clear that it is possible to prevent the development of stenosis and/or maintain pulmonary membrane integrity by inhibiting the expression of adhesion molecules. In particular, however, until now, no substances were available with which the development of coronary heart disease or primary graft failure, or damage to the heart muscle during cardioplegia, could be prevented purposefully and causally via this mechanism.

The inventors have developed, for the first time, a nucleic acid molecule with which this is possible. A nucleic acid molecule which comprises the nucleotide sequences SEQ ID No. 1 and No. 2, No. 3 and No. 4, No. 5 and No. 6, No. 7 and No. 8, No. 9 and No. 10, No. 11 and No. 12 or No. 13 and No. 14 from the accompanying sequence listing surprisingly leads, when inserted in a biological cell, to inhibition of expression of the so-called intracellular adhesion molecule 1 (ICAM-1; CD 54).

A nucleic acid molecule which comprises the nucleotide sequences SEQ ID No. 15 and No. 16, No. 17 and No. 18, No. 19 and No. 20, No. 21 and No. 22, No. 29 and No. 30, No. 31 and No. 32, No. 33 and No. 34 or No. 35 and No. 36 from the accompanying sequence listing, surprisingly leads after insertion in a biological cell to inhibition of expression of the so-called vascular cell adhesion molecule 1 (VCAM-1; CD 106).

A nucleic acid molecule which comprises the nucleotide sequences SEQ ID No. 23 and No. 24, No. 25 and No. 26, No.

27 and No. 28, No. 37 and No. 38, No. 39 and No. 40, No. 41 and No. 42, No. 43 and No. 44 from the accompanying sequence listing, surprisingly leads, when it is inserted in a biological cell, to inhibition of expression of the endothelial adhesion protein E-selectin (CD-62E).

It is known that expression of these genes is (partly) responsible for the development of graft stenosis after transplantation of venous vessels; cf. Chello et al. (loc. cit.). It is also known that expression of these genes is connected with damage to lung transplants; cf. DeMeester et al. (loc. cit.); Egan et al. (loc. cit.); Shreeniwas et al. (1996), Adhesion Molecules (E-Selectin and ICAM-1) in Pulmonary Allograft Rejection, Chest, 110 (5), p. 1143-1149. In the prior art, however, it has not yet been possible to develop means or substances for applying this knowledge therapeutically.

However, the inventors were able to show that by means of a nucleic acid molecule, such as an siRNA molecule, comprising for example two of the aforementioned sequences, by inhibiting the expression of adhesion molecules in the vessels of the organ to be transplanted or to be treated, the patency rate after transplantation or conclusion of a cardioplegic heart operation is increased significantly, or membrane integrity is largely preserved, if corresponding molecules were transfected into the cells.

Such molecules can be used for example during a bypass operation. Thus, segments of the vena saphena explanted during the operation can be stored for about one hour, for example in a Ringer-lactate solution, until used as bypass graft. This phase can be utilized for transfecting the endothelial cells of the vessel with the nucleic acid molecules as siRNA. So-called siRNA molecules of a great many kinds are transfected in the form of a "cocktail" into the cells. The correspondingly treated vessel segments can then be transplanted as bypass. The restenosis rate in the bypass transplant is reduced significantly through inhibition of expression of adhesion molecules in the biological cells.

The molecules according to the invention can also be used during a lung transplant operation. After organ removal, the lung is irrigated with a preserving solution and stored on ice for about six to eight hours until reimplantation in the recipient. This phase can be utilized for transfection of the endothelial cells of the lung, i.e. the pulmonary microvascular cells, with the nucleic acid molecules as siRNA. As already mentioned, various siRNA molecules can be prepared in the form of a cocktail, optionally adding a usual preserving solution, e.g. Euro Collins, Perfadex. It is advantageous if the known transplantation algorithms are not altered.

Furthermore, the molecules according to the invention can be used during cardioplegic open-heart surgery. For this, the molecules according to the invention, for example as siRNA molecules and optionally in the form of a cocktail, are added to the cardioplegic solution.

The inventors have therefore transferred the principle of gene silencing, as already described in the state of the art in other contexts, to the treatment of venous and lung transplants and cardioplegia. For example, Nedbal et al. (2002), Antisense-mediated inhibition of ICAM-1 expression: a therapeutic strategy against inflammation of human periodontal tissue, Antisense & Nucleic Acid Drug Dev. 12(2), pages 71-78, describe the use of antisense oligonucleotides, directed against ICAM-1, for the treatment of periodontal inflammation.

Nishiwaki et al. (2003), Introduction of short interfering RNA to silence endogenous E-selectin in vascular endothelium leads to successful inhibition of leucocyte adhesion, Biochem. Biophys. Res. Commun. 310(4), pages 1062-1066, describe siRNA molecules that are directed against E-selectin and prevent the adhesion of leukocytes to the endothelium.

Elbashir et al. (2001), Duplexes of 21-nucleotide RNAs mediate RNA interference in cultured mammalian cells, Nature 410 (6836), pages 494-498, describe various siRNA molecules with which endogenous and heterologous genes can be suppressed in various mammalian cell lines.

In US 2004/0220129 A1, siRNA molecules are described which are directed against ICAM-1 and are proposed for use for the treatment of inflammatory and autoimmune diseases, diabetes and cancer.

WO 2004/045543 describes a large number of siRNA molecules without concretely stating fields of use or clinical applications.

WO 2004/065546 A2 describes siRNA molecules that are directed against ICAM-1 and are proposed for use for the treatment of inflammatory and autoimmune diseases and diabetes.

WO 03/099298 A2 gives a general description of siRNA-technology though without describing actual molecules.

A survey of current use of siRNA technology is given in Wadhwa et al. (2004), Knowhow of RNA interference and its applications in research and therapy, Mutat. Res. 567(1), pages 71-84.

The invention covers not only such a nucleic acid molecule comprising the sequences SEQ ID No. 1 to No. 44, but also such a nucleic acid molecule which, along with one or more of the stated nucleotide sequences, has additional nucleotides or compounds in the 5' or 3' direction. This does not have any adverse effect on the functionality of the nucleic acid molecule as siRNA molecule. Conversely, by adding additional nucleotides or compounds, the efficacy of the molecule can be increased, for example with nucleotide sequences that promote uptake of the nucleic acid molecule into the biological cells to be treated, or impart nuclease resistance. Moreover, individual nucleotides can be exchanged or mutated within nucleotide sequences SEQ ID No. 1 to SEQ ID No. 44, without the molecule losing the capacity to bind to an essentially complementary nucleotide sequence. Thus, it is decisive for the nucleic acid molecule according to the invention to be hybridized under substantially stringent conditions to an essentially complementary nucleic acid molecule, such as a corresponding mRNA, over sufficiently long segments, leading, via the activity of the assembled RISC—in the case when an siRNA molecule is used—to cleavage of the corresponding mRNA. "Stringent conditions" means, in this context, conditions in which a nonspecific clustering of nucleic acid molecules is prevented. Said stringent conditions are created, for example, by providing a sufficiently high salt concentration, a particular pH value, high temperatures, etc. In these conditions, nucleic acid strands that are able to form base pairs over a sufficient length hybridize with one another.

The nucleic acid molecule according to the invention, which is for example a constituent of an siRNA, can then also be modified so that the nuclease resistance within the cell is increased. Short overhangs at both ends of the strand, which can comprise DNA dimers, have for example proved suitable for this. Deoxythymidines (dt) which can be provided repeatedly preferably at the 3' end, though also at the 5' end, of the nucleic acid molecule according to the invention are especially suitable.

The nucleic acid molecule according to the invention can be produced easily by methods of synthesis that are known in the prior art, cf. Kretschmer-Kazemi Far R. and Sczakiel G. (2003), The activity of siRNA in mammalian cells is related to structural target accessibility: a comparison with antisense oligonucleotides, Nucleic Acids Res. 31(15), pages 4417 to 4424. The contents of this publication are incorporated in the present application by reference.

The accompanying sequence listing gives the nucleotide sequences for the case when the nucleic acid molecule according to the invention is an RNA molecule. It can, of course, also be a DNA molecule. In the latter case, in the nucleotide sequences SEQ ID No. 1 to 44, the "u" (for uracil) is to be replaced in each case with "t" (for thymine). Sequences modified in this way are covered according to the invention by the sequences SEQ ID No. 1 to 44.

Against this background, the present invention also relates to a nucleic acid molecule that is hybridized under stringent conditions to the same nucleic acid molecule to which the nucleic acid with at least one of the nucleotide sequences SEQ ID No. 1 to SEQ ID No. 44 from the accompanying sequence listing hybridizes.

The inventors have developed a therapeutically valuable nucleic acid molecule or various nucleotide sequences, which enable a person skilled in the art to produce further molecules or sequences with comparable properties by routine methods of synthesis without great expenditure, or to modify the stated molecules or sequences optionally by adding and replacing individual nucleotides. Such a further or modified nucleic acid molecule still hybridizes, however, possibly with slight losses that can be tolerated, to the same nucleic acid molecule to which one of the nucleotide sequences SEQ ID No. 1 to 44 hybridizes, and thus equally accomplishes the task according to the invention. Such an optionally modified nucleic acid molecule is accordingly also a subject-matter of the invention.

The present invention further relates to a genetic construct, which comprises the nucleic acid molecule described above and is suitable for the transfection of biological cells, preferably endothelial cells, including pulmonary microvascular cells.

Such a genetic construct is characterized in that, in addition to one or more of the nucleotide sequences SEQ ID No. 1 to SEQ ID No. 44 or sequences derived therefrom, it comprises further nucleotide sequences which favour insertion of the construct into biological cells, for example by transfection. These further nucleotide sequences or segments that serve for transfection are known to a person skilled in the art.

Examples thereof are promoters for RNA polymerase, such as U6 or H1; cf. Brummelkamp et al. (2002), A system for stable expression of short interfering RNAs in mammalian cells. Science 296:550-553; or Lee et al. (2002), Expression of small interfering RNAs targeted against HIV-1 rev transcripts in human cells. Nat. Biotechnol. 20:500-505, or Miyagishi and Taira (2002), Development and application of siRNA expression vector, Nucleic Acids Res. [Suppl] 2002: 113-114. The contents of these publications are incorporated in the present application by reference.

With such a molecule, the suitability as transfection molecule is further optimized. The genetic construct is therefore suitable quite especially as a therapeutic tool for inhibition of the expression of adhesion molecules.

The genetic construct is preferably designed in such a way as to promote transfection of endothelial cells including pulmonary microvascular cells. These cells in fact play a key role in the development of stenosis or damage to vessel membranes for example in transplants. Increased expression of adhesion molecules in these cells leads, among other things, to transendothelial migration of leukocytes, which has an adverse effect on the integrity of the endothelium and may lead to the development of stenotic states or of PGF. This is rectified effectively by the present invention. As was established by the inventors, inhibition of expression of the adhesion molecules blocks the transendothelial migration of leukocytes, so that there are no longer any proinflammatory stimuli for hyperplasia.

The genetic construct is preferably selected from the group consisting of RNA molecule, DNA molecule, plasmid, vector, virus. These molecules can be single-stranded or double-stranded and can optionally form hairpin structures. The term "genetic construct" also includes, according to the invention, a molecule mentioned previously, which forms a complex with calcium phosphate. This measure has the advantage that the nucleic acid molecule or genetic construct can be inserted into the biological cells particularly easily by the so-called calcium phosphate precipitation method.

The present invention therefore also relates to a siRNA molecule that has a pair of RNA molecules, which are hybridized to one another at least partially, and they each have nucleotide sequences that are selected from the group comprising: SEQ ID No. 1 and 2; SEQ ID No. 3 and 4; SEQ ID No. 5 and 6; SEQ ID No. 7 and 8; SEQ ID No. 9 and 10; SEQ ID No. 11 and 12; SEQ ID No. 13 and 14; SEQ ID No. 15 and 16; SEQ ID No. 17 and 18; SEQ ID No. 19 and 20; SEQ ID No. 21 and 22; SEQ ID No. 23 and 24; SEQ ID No. 25 and 26; SEQ ID No. 27 and 28; SEQ ID No. 29 and 30; SEQ ID No. 31 and 32; SEQ ID No. 33 and 34; SEQ ID No. 35 and 36; SEQ ID No. 37 and 38; SEQ ID No. 39 and 40; SEQ ID No. 41 and 42; and SEQ ID No. 43 and 44.

As was discovered by the inventors, these siRNA molecules are particularly powerful tools for inhibition of the expression of adhesion molecules and can therefore be used for the treatment of vessels, preferably venous vessels that are to be transplanted.

Preferably, siRNA molecules are provided that are stabilized against RNAses. This measure has the advantage that the molecules then have a substantially longer life. For example, with stabilized siRNA molecules, the stability in the serum increases to hours, as opposed to minutes in the case of unstabilized siRNA molecules. To obtain stabilized siRNA molecules, the latter are chemically modified by methods known to a person skilled in the art. Such methods are marketed for example by the company Dharmacon, Inc., Chicago, USA, with the name siSTABLE™ v2, or by the company Atugen, Berlin, Germany, with the name AtuRNAi. Stabilized siRNA molecules are also described in Morrissey et al. (2005), Potent and persistent in vivo anti-HBV activity of chemically modified siRNAs, Nat. Biotechnol. 23(8), pages 1002 to 1007; Chiu et al. (2003), siRNA Function in RNAi: A chemical modification analysis, RNA 9(9), pages 1034-1048; the contents of these publications are incorporated in the present application by reference.

The siRNA molecule is preferably a hairpin siRNA molecule. These hairpin siRNA molecules are incorporated into the DNA of the recipient cell and there is then permanent expression of the siRNA in the cell. This measure has the advantage that expression of the adhesion molecules is inhibited permanently, as the inhibiting siRNA molecules are constantly "replenished".

The present invention further relates to a composition that comprises at least one of the nucleic acid molecules described previously, and/or the genetic construct described previously and/or the aforementioned siRNA molecule. The composition is preferably a physiological solution for the incubation or preservation of organs, preferably blood vessels or lung transplants, which comprises a buffer substance, salts and other auxiliaries, actives, additives or preservatives if required.

The explanted organ, i.e. for example the venous vessel to be transplanted or the lung transplant, can be placed in such a composition during or after the operation; the composition can also be a cardioplegic solution, containing potassium and magnesium. Then the actual transfection of the nucleic acid molecules and/or genetic constructs or siRNA molecules contained therein into the cells of the vessel, transplant or the open heart can be carried out with or in this composition. As mentioned above, the composition can contain a mixture of the nucleic acid molecules or siRNA molecules according to the invention and thus prevent the inhibition of a great variety of adhesion molecules. Auxiliaries or additives serve to ensure that the organs are stored and/or preserved as carefully as possible, and are known to a person skilled in the art. These also include transfection-mediating substances, for example Cellfectin, Lipofectamine, Optifect from the company Invitrogen GmbH, Karlsruhe, Germany. Preservatives are also known to a person skilled in the art, which prevent the growth of contaminating microorganisms and can for example comprise antibiotics. The latter can also serve as selection agents for verifying successful transfection. The provision of actives, for example additional therapeutically active substances, has the advantage that the organ can be pretreated therapeutically in other additional ways in parallel with transfection, which can additionally improve the lasting suitability of the transplant as bypass or respiratory organ. The aforementioned substances and salts are also certainly known to a cell biologist or a specialist in transplantation medicine.

The present invention further relates to a device, in particular a stent, which has a coating, characterized in that the coating contains the nucleic acid molecule and/or genetic construct and/or siRNA molecule and/or composition described above.

Stents, generally in the form of small tubes of metal-wire mesh, are used for permanently dilating blocked or narrowed vessels and hence for increasing the diameter of the vessel lumen and for preventing collapse of the vessel or sudden reocclusion. A stent is thus a flexible, tubular latticework, which supports the vessel for improved patency of blood vessels, especially in the heart.

Coated stents according to the invention, which are positioned appropriately, for example using a balloon catheter, in the vessel to be treated, can be prepared so that the nucleic acid molecules or siRNA molecules etc. contained in the coating are released as a "drug release" or "drug eluting" effect to the surrounding vessel, where they exert their therapeutic action. Stents of the kind according to the invention can provide locally limited application of the nucleic acid molecules. The coating used for this can comprise liposomal nanoparticles, into which the nucleic acid molecules according to the invention are incorporated in a stable manner by physicochemical methods known to a person skilled in the art, and are released, with a time delay if required, to the vessel to be treated.

It is preferable according to the invention for the coating of the device or of the stent to be formed from biodegradable and/or bioresorbable polymers. Such biomaterials are established for surgical applications and are known to a person skilled in the art. Suitable biomaterials include polysulphones (PSU), polyether sulphones (PESU), polyglycolides and polylactides, for example poly(DL-lactide-co-glycolide) (PLGA), magnesium and mixtures thereof. These materials are particularly suitable as coating materials for stents. On the one hand they ensure preservation of the mechanical properties of the stent and improvement of their biocompatibility through the coating. On the other hand the polymer can also contain the nucleic acid molecules or siRNA molecules according to the invention. Such a polymer can then be used as a matrix for the targeted release of the siRNA molecules, which then inhibit expression of the corresponding adhesion molecules. In this context they can be called "gene-silencing stents". The biodegradable polymer remains available in the body for at least as long as siRNA molecules are eluted. This ensures that the integrity of the vessel being treated remains unimpaired not only during the operation, but also for a certain length of time after reimplantation in the recipient.

Alternatively, the stents can be formed from these biomaterials entirely, which then contain the nucleic acid molecules and/or siRNA molecules according to the invention. These resorbable stents have the advantage that they leave the natural vessel architecture intact and, for example, also do not deprive the heart surgeon of any attachment points for bypasses. In some circumstances, resorbable stents also permit so-called plug-sealing, i.e. the prophylactic stenting of stenoses that are not haemodynamically relevant when unstable plugs are detected. Modern imaging can show such structures with increasing clarity. A review of bioresorbable stents, and magnesium stents in particular, can be found in Erne et al. (2005), The Road to Bioabsorbable Stents: Reaching Clinical Reality? Cardiovasc. Intervent. Radiol. 29; the contents of this publication are incorporated in the present application by reference.

Against this background, the present invention also relates to the use of the nucleic acid molecule that comprises one of the nucleotide sequences SEQ ID No. 1 to 44 or of a nucleic acid molecule which hybridizes under stringent conditions to the same nucleic acid molecule, as siRNA or for the production of the latter.

The inventors have recognized, for the first time, that a nucleic acid molecule with the stated nucleotide sequences can be used for "gene silencing" and as a result inhibition of the expression of endothelial adhesion molecules is effected preferentially. According to the invention, a nucleic acid molecule that comprises the nucleotide sequences SEQ ID No. 1 and 2, No. 3 and 4, No. 5 and 6, No. 7 and 8, No. 9 and 10, No. 11 and 12 and No. 13 and 14 from the accompanying sequence listing, or a nucleic acid molecule with comparable hybridization properties, is used for inhibition of the endothelial expression of ICAM-1. The same applies correspondingly to a nucleic acid molecule with the nucleotide sequence SEQ ID No. 15 and 16, No. 17 and 18, No. 19 and 20, No. 21 and 22, No. 29 and 30, No. 31 and 32, No. 33 and 34; and No. 35 and 36 for inhibition of the endothelial expression of VCAM-1, and to a nucleic acid molecule with the nucleotide sequences SEQ ID No. 23 and 24, No. 25 and 26, No. 27 and 28, No. 37 and 38, No. 39 and 40, No. 41 and 42; and No. 43 and 44 for inhibition of the endothelial expression of E-selectin (C62-E).

As already explained, a nucleic acid molecule with comparable hybridization properties is to be understood as one that is derived from the nucleotide sequences SEQ ID No. 1 to 44 and functions equally as an siRNA molecule, possibly at the expense of small losses of activity. Thus, the inventive feat does not in fact comprise providing a specific nucleotide sequence, which is then to be converted in an identical manner to a corresponding nucleic acid molecule, but rather in providing basic sequences that serve as guiding structures for corresponding nucleic acid molecules with siRNA properties. Therefore the present invention is not limited to nucleic acid molecules that consist exclusively of one of the nucleotide sequences SEQ ID No. 1 to 44. Rather it includes nucleic acid molecules that comprise sequences that are derived from the stated sequences and have comparable hybridization properties under stringent conditions.

The present invention further relates to a method for inhibition of the expression of adhesion molecules in biological cells, which comprises the following steps: (a) provision of the biological cells, preferably of organs or parts of organs, and more preferably of blood vessels, (b) insertion of the previously described nucleic acid molecule or genetic construct or siRNA molecules into the biological cells, and optionally (c) washing and/or isolation of the biological cells.

According to the invention, step (b) is accomplished for example by usual transfection methods, for example calcium phosphate precipitation, electroporation, microinjection, lipofection, polyfection by means of dendrimers, receptor-mediated transfer etc.; cf. for example Sambrook, J. and Russell D. W. (2001), Molecular Cloning—Laboratory Manual, Cold Spring Harbor Laboratory Press; the contents of this publication are incorporated in the present application by reference.

With this method it is possible, by simple means, both for isolated biological cells and for organs or parts of organs, such as vessel segments or lung transplants, to be treated ex vivo so that the expression of adhesion molecules, which are associated with the occlusion of bypass grafts, is inhibited in the corresponding cells. With this method, therefore, the cell biologist or the physiologist and the surgeon are provided with a special method by which precise (pre-) treatment of biological cells or organ parts can be carried out. The cells or organ parts so treated can be used for scientific investigations relating to cell biology as well as for subsequent transplantation, for example as bypass or lung.

In this method it is preferable for the insertion in step (b) to be effected by means of non-viral transient transfection.

This measure has the advantage that the infectiological component of viral vectors is absent from this form of transfection. Non-viral transient transfection is likewise extremely efficient and can be carried out by known molecular-biological measures, during a heart operation as well.

The inventors have also developed a vessel transplantation method that can be carried out on a patient and comprises the following steps: (a) removal of a vessel, preferably the vena saphena magna, from the patient, (b) insertion of the nucleic acid molecule as described above or of the genetic construct or of the siRNA molecules into the cells of the vessel, preferably by non-viral transient transfection, and (c) transplantation or implantation of the treated vessel, preferably for the production of a bypass.

In contrast to the vessel grafting techniques carried out hitherto, this has the advantage that by the treatment of the vessel, by insertion of the nucleic acid molecules or genetic constructs or siRNA molecules, the expression of adhesion molecules is inhibited in its endothelial cells. The subsequently transplanted vessel shows a far lower restenosis rate, compared with untreated grafts. During incubation according to step (b) transfection of the endothelial cells is carried out for example by non-viral liposomal transfection. This leads to transient protection of the bypass graft, which, especially during the first critical hours of the reperfusion phase, provides protection of the bypass endothelium and thus contributes to a decrease in the early restenosis rate.

Against this background, step (c) takes place after conclusion of step (a) in a time interval of up to five hours, preferably at most one hour.

This measure has the advantage of ensuring that the vessel removed does not suffer any loss of vitality, but rather, its physiological functions are fully maintained. Minimal losses of vitality can, however, be tolerated.

Until now there has been no clinically practicable therapeutic means for blocking endothelial adhesion molecule expression and therefore protecting vessel transplants. In the state of the art there are isolated descriptions of experimental approaches in which protection of vessel transplants is envisaged by means of the application of antibodies against adhesion molecules or by hyperthermally induced release of heat-shock proteins that have a protective action. However, such approaches have proved to be not convertible, or as pharmacologically extremely problematically convertible.

The inventors therefore provide an important tool and method that can be used for the treatment of coronary heart disease and in particular can be integrated optimally into surgical OP-management in bypass operations.

The inventors have in addition developed a lung transplantation technique that can be carried out on a patient and comprises the following steps: (a) removal of the lung from a donor, (b) insertion of the nucleic acid molecule as described above or of the genetic construct or of the siRNA molecule into the pulmonary microvascular cells, preferably by means of non-viral transient transfection, and (c) transplantation or implantation of the lung into the patient. The donor can be either a beating-heart donor (BHD) or a non-heart-beating donor (NHBD).

Step (c) preferably takes place after conclusion of step (a) after a time interval of about six to eight hours. This measure has the advantage that the period of storage of the lung in a preserving solution is utilized optimally for the transfection of the siRNA molecules.

The present invention further relates to a method of lung transplant treatment or preservation comprising the following steps: (a) preparing a lung transplant, and (b) insertion of the nucleic acid molecule as described above or of the genetic construct or of the siRNA molecule into the pulmonary microvascular cells, preferably by means of non-viral transient transfection.

The invention further relates to a method for open-heart treatment within the scope of cardioplegia, comprising the following steps: (a) preparation of an open-heart patient, (b) insertion of the nucleic acid molecule as described above or of the genetic construct or of the siRNA molecule into the endothelial cells of the heart, preferably by means of non-viral transient transfection.

The present invention will now be explained on the basis of examples of application, which are purely for purposes of illustration and do not limit the scope of the invention in any way. Reference will be made to the appended drawings, showing the following:

EMBODIMENTS

Nucleic Acid Molecules

Figure 1:
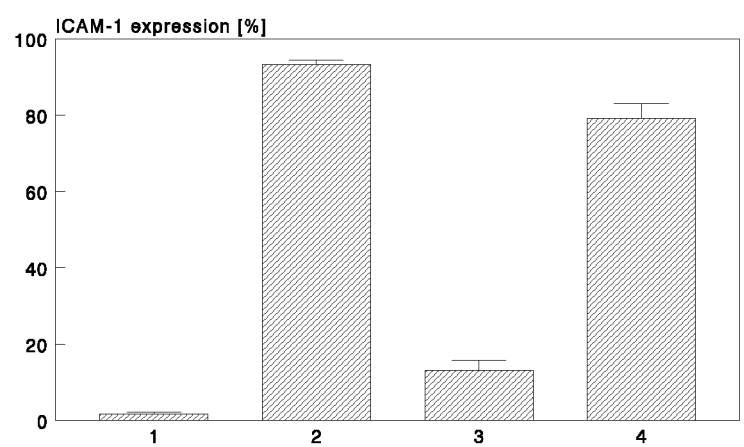
FIG. 1 shows the result of an analysis by flow cytometry, with which the inhibition of ICAM expression in endothelial cells was achieved by means of nucleic acid molecules according to the invention.

The nucleic acid molecules used in the experiments that led to the invention were synthesized as oligonucleotides by processes that are familiar to a person skilled in the art. To form a double-stranded siRNA molecule, a sense strand is hybridized with the respective antisense strand in conditions that are known in the state of the art.

The synthesis of the oligonucleotides and the formation of siRNA is described for example in Kretschmer-Kazemi (loc. cit.), in particular in the part relating to materials and methods, said part being incorporated in the present application by reference.

The following table presents an overview of the nucleic acid molecules used according to the invention:

TABLE 1

Nucleic acid molecules according to the invention

| siRNA | Target | Oligonucleotides | SEQ ID No. |
|---|---|---|---|
| 1 | ICAM-1 | 5'-GCCUCAGCACGUACCUCUA-3' (sense) | 1 |
|   |        | 5'-UAGAGGUACGUGCUGAGGC-3' (antisense) | 2 |
| 2 | ICAM-1 | 5'-CCCUUGAUGAUAUGUAUUU-3' (sense) | 3 |
|   |        | 5'-AAAUACAUAUCAUCAAGGG-3' (antisense) | 4 |
| 3 | ICAM-1 | 5'-GCCAGCUUAUACACAAGAA-3' (sense) | 5 |
|   |        | 5'-UUCUUGUGUAUAAGCUGGC-3' (antisense) | 6 |
| 4 | ICAM-1 | 5'-GAUCAAGAAAUACAGACUA-3' (sense) | 7 |
|   |        | 5'-UAGUCUGUAUUUCUUGAUC-3' (antisense) | 8 |
| 5 | ICAM-1 | 5'-CAAGAAAUACAGACUACAA-3' (sense) | 9 |
|   |        | 5'-UUGUAGUCUGUAUUUCUUG-3' (antisense) | 10 |
| 6 | ICAM-1 | 5'-AGACUACAACAGGCCCAAA-3' (sense) | 11 |
|   |        | 5'-UUUGGGCCUGUUGUAGUCU-3' (antisense) | 12 |
| 7 | ICAM-1 | 5'-GUCAGAUACAACAGCAUUU-3' (sense) | 13 |
|   |        | 5'-AAAUGCUGUUGUAUCUGAC-3' (antisense) | 14 |
| 8 | VCAM-1 | 5'-GAUAGAUAGUCCACUGAAU-3' (sense) | 15 |
|   |        | 5'-AUUCAGUGGACUAUCUAUC-3' (antisense) | 16 |
| 9 | VCAM-1 | 5'-GGAUACGGAUAUGAAAUCU-3' (sense) | 17 |
|   |        | 5'-AGAUUUCAUAUCCGUAUCC-3' (antisense) | 18 |
| 10 | VCAM-1 | 5'-GUACGCAAACACUUUAUGU-3' (sense) | 19 |
|    |        | 5'-ACAUAAAGUGUUUGCGUAC-3' (antisense) | 20 |
| 11 | VCAM-1 | 5'-AAUGCAACUCUCACCUUAA-3' (sense) | 21 |
|    |        | 5'-UUAAGGUGAGAGUUGCAUU-3' (antisense) | 22 |
| 12 | E-Selectin | 5'-GACCAUCAAUAAUUACACU-3' (sense) | 23 |
|    |            | 5'-AGUGUAAUUAUUGAUGGUC-3' (antisense) | 24 |
| 13 | E-Selectin | 5'-ACGUGUAAAGCUGUGACAU-3' (sense) | 25 |
|    |            | 5'-AUGUCACAGCUUUACACGU-3' (antisense) | 26 |
| 14 | E-Selectin | 5'-UUAAAGAGAGUGGAGCCUGGU-3' (sense) | 27 |
|    |            | 5'-ACCAGGCUCCACUCUCUUUAA-3' (antisense) | 28 |
| 15 | VCAM-1 | 5'-GGAGGAUACGGAUAUGAAA-3' (sense) | 29 |
|    |        | 5'-UUUCAUAUCCGUAUCCUCC-3' (antisense) | 30 |
| 16 | VCAM-1 | 5'-GAGCUAAAUUACACAUUGA-3' (sense) | 31 |
|    |        | 5'-UCAAUGUGUAAUUUAGCUC-3' (antisense) | 32 |
| 17 | VCAM-1 | 5'-CAUCUACGCUGACAAUGAA-3' (sense) | 33 |
|    |        | 5'-UUCAUUGUCAGCGUAGAUG-3' (antisense) | 34 |
| 18 | VCAM-1 | 5'-CUCUAUAUUUAGAUUGUUA-3' (sense) | 35 |
|    |        | 5'-UAACAAUCUAAAUAUAGAG-3' (antisense) | 36 |
| 19 | E-Selectin | 5'-GGUUGAAUGCACCACUCAA-3' (sense) | 37 |
|    |            | 5'-UUGAGUGGUGCAUUCAACC-3' (antisense) | 38 |
| 20 | E-Selectin | 5'-UGGUAGAAUUGGAGAGUAA-3' (sense) | 39 |
|    |            | 5'-UUACUCUCCAAUUCUACCA-3' (antisense) | 40 |
| 21 | E-Selectin | 5'-CAGUGUGGUUUGUGUUUGA-3' (sense) | 41 |
|    |            | 5'-UCAAACACAAACCACACUG-3' (antisense) | 42 |
| 22 | E-Selectin | 5'-CGGAAGCUAUGACUUAUGA-3' (sense) | 43 |
|    |            | 5'-UCAUAAGUCAUAGCUUCCG-3' (antisense) | 44 |
| 23 | Negative control | 5'-UUCUCCGAACGUGUCACGU-3' (sense) | 45 |
|    |                  | 5'-ACGUGACACGUUCGGAGAA-3' (antisense) | 46 |

Patients

Vessel samples, i.e. sections of the vena saphena magna, were obtained from patients who had undergone coronary artery bypass grafting (CABG). These sections are usually discarded after such an operation. The patients had previously given their consent to the scientific use of the vessel section.

The experiments had been approved beforehand by the ethical committee of Tübingen University.

Isolation and Cultivation of the Endothelial Cells from the Vena Saphena Magna

The cells were obtained and cultivated in accordance with previously published protocols; cf. Nachman, R. L. and Jaffe, E. A. (2004), Endothelial cell culture: beginnings of modern vascular biology, J. Clin. Invest. 114(8), pages 1037-1040, and Jaffe et al. (1973), Culture of human endothelial cells derived from umbilical veins. Identification by morphologic and immunologic criteria, J. Clin. Invest. 52(11), pages 2745-2756.

Briefly, all culture plates and flasks (Becton Dickinson GmbH, Heidelberg, Germany) were coated overnight with 40% collagen (Collagen G, Biochrom, Indiana, USA). The complete vein was first incubated in RPMI 1640 buffer (Cambrex Bio Science Verviers, S.p.r.l., Verviers, Belgium) and 0.5%/ml gentamycin (Invitrogen GmbH, Karlsruhe, Germany). Then the vein was rinsed with buffer (137 mM in NaCl, 5.4 mM KCl, 4.2 mM $NaHCO_3$, 5 mM D-glucose in 500 ml $H_2O$, pH 7.3, sterile). The endothelial cells were obtained by digestion with 0.1% collagenase (PAA Laboratories GmbH, Cölbe, Germany) in phosphate-buffered saline (PBS) and further cultivation in EGM-2 (+bullet kit, Cambrex Bio Science Verviers). After attaining confluence, the cells were separated from one another by treatment with trypsin (Detach Kit, PromoCell GmbH, Heidelberg, Germany). Cells from the third passage were used for all the experiments. To verify absence of contamination by mycoplasmae, tests were carried out using the DAPI method (SERVA Elektrophoresis GmbH, Heidelberg, Germany). The purity of the isolated venous endothelial cells was verified by staining against the Willebrand Factor, VEGFR-2, Tie-2.

Pulmonary Microvascular Cells

The human pulmonary microvascular cells were obtained from Cambrex Bio Science Wokingham, Ltd., Berkshire, England.

Transfection of the Isolated Endothelial Cells

All transfections were carried out in RNAse-free conditions. The isolated endothelial cells were cultivated in collagenized 12-well plates (Greiner Bio-One GmbH, Frickenhausen, Germany) without antibiotics. After attaining confluence (70-80%), the isolated endothelial cells were transfected with hybridized siRNA using 2.01 µl/ml Cellfectin (Invitrogen GmbH, Karlsruhe, Germany). Four different cell treatments, each in duplicate, were tested in parallel: 1. non-stimulated isolated endothelial cells/pulmonary microvascular cells, non-transfected; 2. stimulated (TNF-α, 2.5 ng/ml or 5 ng/ml) isolated endothelial cells/pulmonary microvascular cells, not transfected; 3. stimulated with siRNA molecules according to the invention, transfected and isolated endothelial cells/pulmonary microvascular cells; 4. stimulated with nonspecific, randomized siRNA (QIAGEN GmbH, Hilden, Germany) transfected and isolated endothelial cells/pulmonary microvascular cells.

The transfection time was 2 hours and the experiments were repeated four times. After 9 hours all the isolated endothelial cells/pulmonary microvascular cells were stimulated with TNF-α (2.5 ng/ml or 5 ng/ml) (Immunotools, Friesoythe, Germany) for 15 hours.

Analysis by Flow Cytometry (Fluorescence-Activated Cell Sorting) (FACS)

After TNF-α stimulation, all the batches of isolated and possibly transfected endothelial cells/pulmonary microvascular cells were washed with EGM-2 medium. The nonspecific binding of antibodies was blocked with FCS (5%, pH 7.4). A PE-labelled antibody against the respective adhesion molecules (Becton Dickinson GmbH, Heidelberg, Germany), i.e. against ICAM-1, VCAM-1 or E-selectin (CD-62E) was used (4° C., 1 hour) for staining the optionally transfected, isolated endothelial cells/pulmonary microvascular cells. After washing and detachment, the cells were fixed with 2.5% paraformaldehyde in PBS. The FACS analyses (5000 cells/measurement) were carried out in a FACS-can™ (Becton Dickinson GmbH, Heidelberg, Germany) and calculated using the CellQuestPro software (Becton Dickinson GmbH, Heidelberg, Germany).

The results of these experiments are presented in FIGS. 1 to 6.

Figure 4:
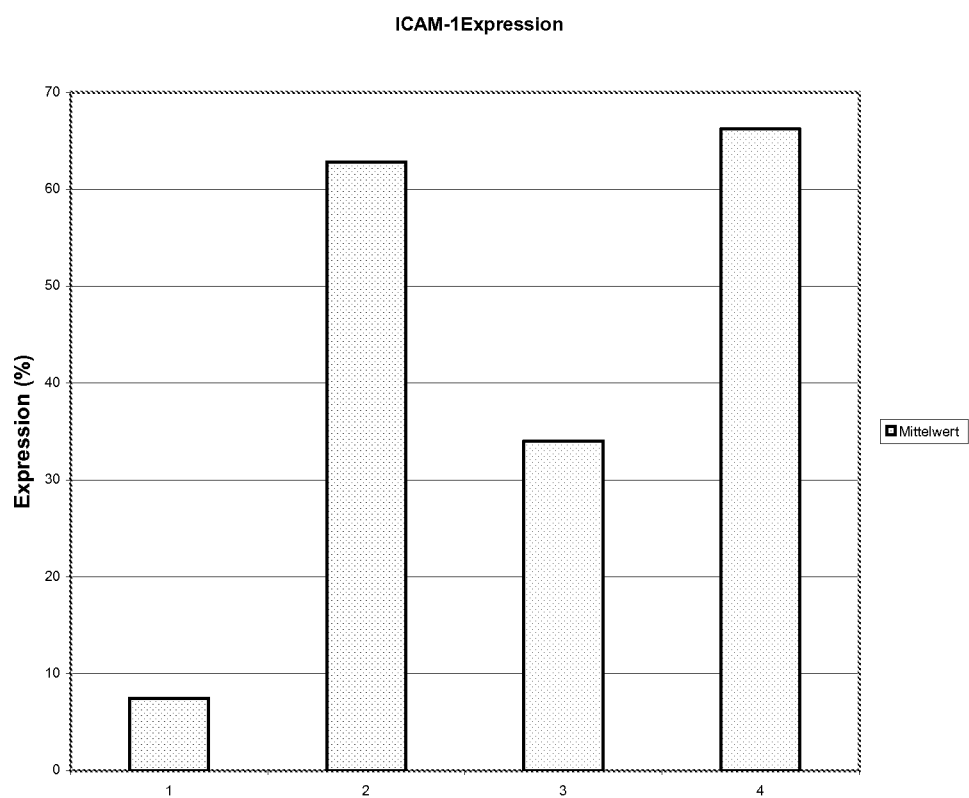
FIG. 4 shows the result of an analysis by flow cytometry, with which the inhibition of ICAM expression in pulmonary microvascular cells from human lungs was achieved by means of nucleic acid molecules according to the invention.

FIGS. 1 and 4 show representative results of the experiments in which the isolated endothelial cells (FIG. 1) or pulmonary microvascular cells (FIG. 4) were transfected with one of the siRNAs according to the invention, which was directed against ICAM-1, i.e. with an siRNA molecule with No. 1 to 7 according to Table 1. In the FACS analysis, the cells were stained correspondingly with an antibody that was directed against human ICAM-1. The result was comparable for each of the siRNA molecules.

Figure 2:
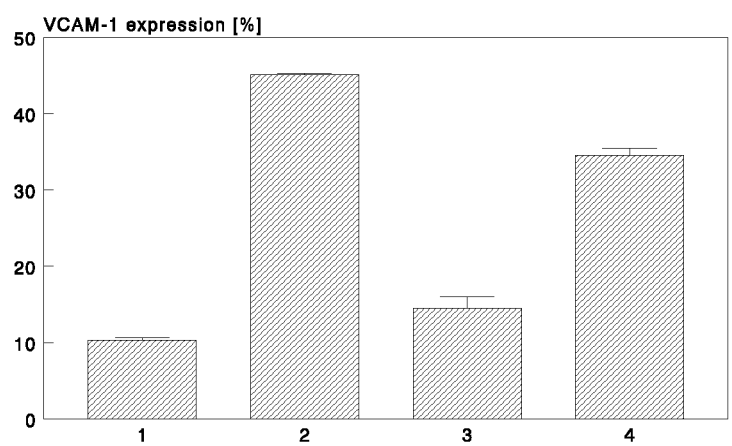
FIG. 2 shows the result of a comparable experiment, in which the inhibition of VCAM-1 expression in endothelial cells was achieved by means of nucleic acid molecules according to the invention.
Figure 5:
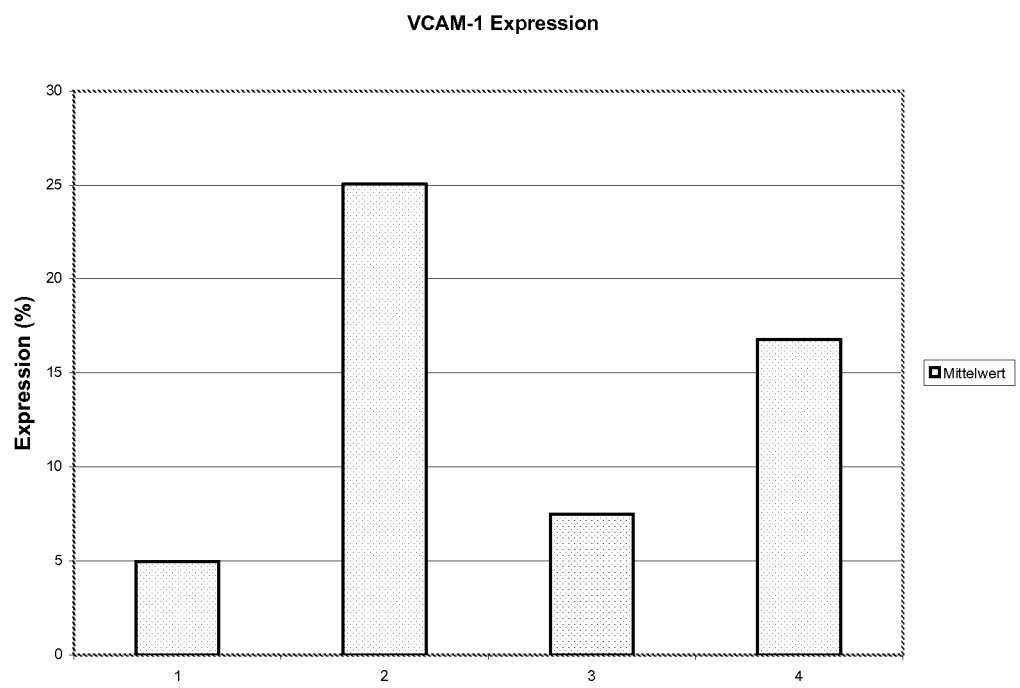
FIG. 5 shows the result of a comparable experiment, in which the inhibition of VCAM-1 expression in pulmonary microvascular cells was achieved by means of nucleic acid molecules according to the invention.

FIGS. 2 and 5 show representative results of the experiments in which the isolated endothelial cells (FIG. 2) or pulmonary microvascular cells (FIG. 5) were transfected with one of the siRNAs according to the invention, which was directed against VCAM-1, i.e. with an siRNA molecule with No. 8 to 11 or 15 to 18 according to Table 1. In the FACS analysis, the cells were stained correspondingly with an antibody that was directed against human VCAM-1. Once again, the result was comparable for each of the siRNA molecules.

Figure 3:
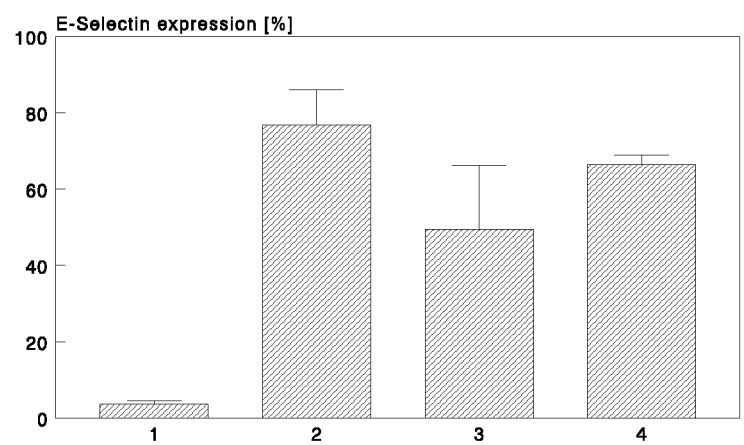
FIG. 3 shows the result of another comparable experiment, in which inhibition of the expression of E-selectin (CD-62E) in endothelial cells was achieved by means of nucleic acid molecules according to the invention.
Figure 6:
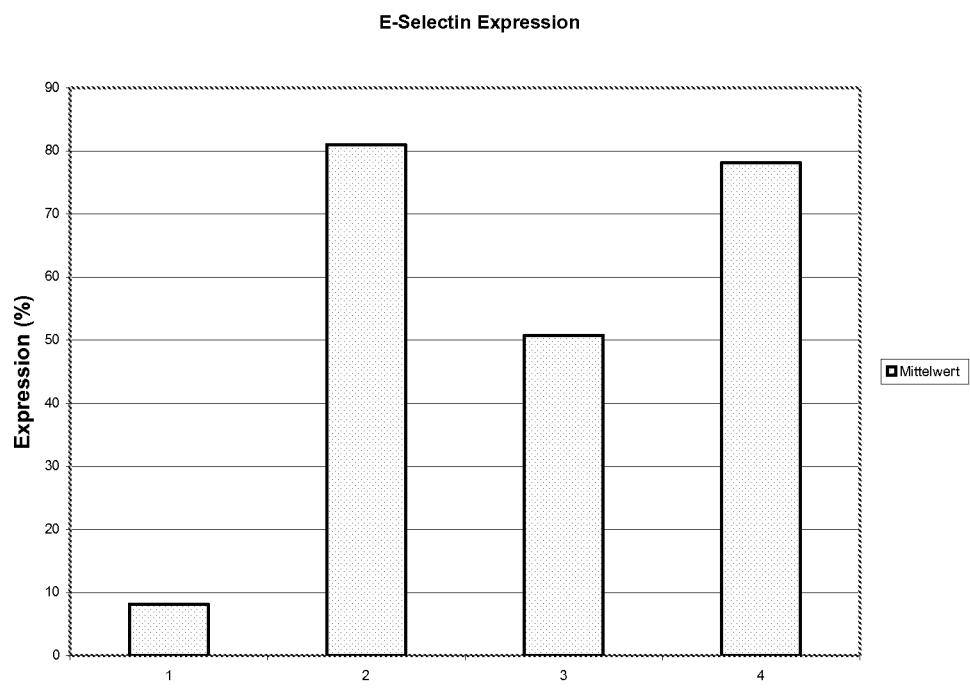
FIG. 6 shows the result of a comparable experiment, in which inhibition of the expression of E-selectin in pulmonary microvascular cells was achieved by means of nucleic acid molecules according to the invention.

FIGS. 3 and 6 show representative results of the experiments in which the isolated endothelial cells (FIG. 3) or pulmonary microvascular cells (FIG. 6) were transfected with one of the siRNAs according to the invention, which was directed against E-selectin, i.e. with an siRNA molecule with No. 12 to 14 or 19 to 22 according to Table 1. In the FACS analysis, the cells were stained correspondingly with an antibody that was directed against human E-selectin. The result was comparable for each of the siRNA molecules.

Assays (1) each show the negative control, i.e. without transfection and without stimulation. Assays (2) each show the positive controls, i.e. without transfection but with stimulation by TNF-α. Assays (3) show the transfections with the specific siRNA in TNF-α stimulated endothelial cells/pulmonary microvascular cells. Assays (4) show controls, in which the endothelial cells/pulmonary microvascular cells were stimulated with TNF-α and transfected with the nonspecific siRNA (No. 23 according to Table 1; SEQ ID No. 45 and No. 46).

It can be seen in all assays (3) that transfection of the cells with specific siRNA according to the invention in the corresponding endothelial cells/pulmonary microvascular cells led to a drastic inhibition of the expression of the respective adhesion molecules (compare with assays (2)).

This inhibition in the endothelial cells was quite especially pronounced in the case of ICAM-1. Here, the level of expression was inhibited by almost 90% by the treatment with the siRNA according to the invention. In the case of VCAM-1 the level of expression was reduced by almost 70%. In the case of E-selectin (CD-62E) the level of expression was reduced by more than 40%.

In the pulmonary microvascular cells, the level of expression of ICAM-1 was inhibited by just 50% by the treatment with the siRNA according to the invention. In the case of VCAM the level of expression was reduced by more than 70%. In the case of E-selectin, a reduction by more than 30% was observed.

The inventors were thus able to demonstrate that the nucleic acid molecules according to the invention are extremely powerful tools for inhibition of the expression of adhesion molecules in biological cells and are therefore particularly suitable for the treatment of transplants.

The invention claimed is:

1. A composition comprising a nucleic acid molecule for inhibiting the expression of intracellular adhesion molecule 1 (ICAM-1), which comprises at least one of the nucleotide sequences according to SEQ ID No. 1, 2, 3, 4, 5, 6, 7, 8, 9, 10, 11, 12, 13, or 14, wherein the composition is a physiological solution for the incubation of organs, and comprises a buffer substance, salts and if necessary, other auxiliaries, actives, additives or preservatives.

2. The composition according to claim 1, wherein the organs comprise venous grafts.

3. The composition according to claim 1, wherein the organs comprise a lung transplant.

4. The composition according to claim 1, wherein the organs comprise an open heart and the physiological solution is designed as a cardioplegic solution.

5. A stent, comprising a coating, wherein the coating comprises a nucleic acid molecule for inhibiting the expression of ICAM1, which comprises at least one of the nucleotide sequences according to SEQ ID No. 1, 2, 3, 4, 5, 6, 7, 8, 9, 10, 11, 12, 13, or 14.

6. The stent according to claim 5, wherein the coating comprises a biodegradable and/or bioresorbable polymer or magnesium.

7. A method of inhibiting expression of intracellular adhesion molecule 1 (ICAM-1) in biological cells of organs, comprising:
   incubating the organs in the composition of claim 1, and optionally
   washing the organs, thereby inhibiting expression of ICAM-1 in the biological cells of the organs.

8. The method according to claim 7, wherein the organs are selected from the group consisting of: venous grafts, a lung transplant, and an open heart.

9. A method of vessel grafting in a patient, comprising:
   (a) removing a vessel from the patient,
   (b) incubating the vessel in the composition of claim 1, thereby inhibiting expression of ICAM-1 in cells of the vessel, and
   (c) transplanting or implanting the treated vessel into the patient, thereby grafting the vessel in the patient.

10. The method according to claim 9, wherein step (c) is carried out after conclusion of step (a), after a period of about one hour at most.

11. A method of lung transplantation in a patient, comprising:
   (a) removing a lung from a donor,
   (b) incubating the lung in the composition of claim 1, thereby inhibiting expression of ICAM-1 in cells of the lung, and
   (c) transplanting or implanting the treated lung into the patient.

12. The method according to claim 11, wherein step (c) is effected after conclusion of step (a) after a period of about six to about eight hours.

13. A method of treating a lung transplant, comprising:
   (a) preparing of a lung transplant, and
   (b) incubating the lung transplant in the composition of claim 1, thereby inhibiting expression of ICAM-1 in cells of the lung and treating the lung transplant.

14. A method of treatment of the open heart within the scope of cardioplegia, comprising:
   (a) preparing an open-heart patient, and
   (b) incubating the open heart in the composition of claim 1, thereby inhibiting expression of ICAM-1 and treating the open heart within the scope of cardioplegia.

15. The composition according to claim 1, wherein the nucleic acid molecule is an siRNA molecule, which comprises a pair of RNA molecules which are hybridized at least partially against one another and which each comprise nucleotide sequences which are selected from the group consisting of: SEQ ID No. 1 and 2; SEQ ID No. 3 and 4; SEQ ID No. 5 and 6; SEQ ID No. 7 and 8; SEQ ID No. 9 and 10; SEQ ID No. 11 and 12; and SEQ ID No. 13 and 14.

16. The composition according to claim 15, wherein the siRNA molecule is a stabilized siRNA molecule.

17. The composition according to claim 15, wherein the siRNA molecule is a hairpin siRNA molecule.

18. The stent according to claim 5, wherein the nucleic acid molecule is an siRNA molecule, which comprises a pair of RNA molecules which are hybridized at least partially against one another and which each comprise nucleotide sequences which are selected from the group consisting of: SEQ ID No. 1 and 2; SEQ ID No. 3 and 4; SEQ ID No. 5 and 6; SEQ ID No. 7 and 8; SEQ ID No. 9 and 10; SEQ ID No. 11 and 12; and SEQ ID No. 13 and 14.

19. The composition according to claim 1, wherein the nucleic acid molecule comprises nucleotide sequences set forth as SEQ ID No. 1 and 2.

* * * * *

```
                            SEQUENCE LISTING

<160> NUMBER OF SEQ ID NOS: 46

<210> SEQ ID NO 1
<211> LENGTH: 19
<212> TYPE: RNA
<213> ORGANISM: Artificial sequence
<220> FEATURE:
<223> OTHER INFORMATION: Description of the artificial sequence:
      oligonucleotide

<400> SEQUENCE: 1
gccucagcac guaccucua                                                        19

<210> SEQ ID NO 2
<211> LENGTH: 19
<212> TYPE: RNA
<213> ORGANISM: Artificial sequence
<220> FEATURE:
<223> OTHER INFORMATION: Description of the artificial sequence:
      oligonucleotide

<400> SEQUENCE: 2
uagagguacg ugcugaggc                                                        19

<210> SEQ ID NO 3
<211> LENGTH: 19
<212> TYPE: RNA
<213> ORGANISM: Artificial sequence
<220> FEATURE:
<223> OTHER INFORMATION: Description of the artificial sequence:
      oligonucleotide

<400> SEQUENCE: 3
cccuugauga uauguauuu                                                        19

<210> SEQ ID NO 4
<211> LENGTH: 19
<212> TYPE: RNA
<213> ORGANISM: Artificial sequence
<220> FEATURE:
<223> OTHER INFORMATION: Description of the artificial sequence:
      oligonucleotide

<400> SEQUENCE: 4
aaauacauau caucaaggg                                                        19

<210> SEQ ID NO 5
<211> LENGTH: 19
<212> TYPE: RNA
<213> ORGANISM: Artificial sequence
<220> FEATURE:
<223> OTHER INFORMATION: Description of the artificial sequence:
      oligonucleotide

<400> SEQUENCE: 5
gccagcuuau acacaagaa                                                        19

<210> SEQ ID NO 6
<211> LENGTH: 19
<212> TYPE: RNA
```

```
<213> ORGANISM: Artificial sequence
<220> FEATURE:
<223> OTHER INFORMATION: Description of the artificial sequence:
      oligonucleotide

<400> SEQUENCE: 6
uucuugugua uaagcuggc                                                      19

<210> SEQ ID NO 7
<211> LENGTH: 19
<212> TYPE: RNA
<213> ORGANISM: Artificial sequence
<220> FEATURE:
<223> OTHER INFORMATION: Description of the artificial sequence:
      oligonucleotide

<400> SEQUENCE: 7
gaucaagaaa uacagacua                                                      19

<210> SEQ ID NO 8
<211> LENGTH: 19
<212> TYPE: RNA
<213> ORGANISM: Artificial sequence
<220> FEATURE:
<223> OTHER INFORMATION: Description of the artificial sequence:
      oligonucleotide

<400> SEQUENCE: 8
uagucuguau uucuugauc                                                      19

<210> SEQ ID NO 9
<211> LENGTH: 19
<212> TYPE: RNA
<213> ORGANISM: Artificial sequence
<220> FEATURE:
<223> OTHER INFORMATION: Description of the artificial sequence:
      oligonucleotide

<400> SEQUENCE: 9
caagaaauac agacuacaa                                                      19

<210> SEQ ID NO 10
<211> LENGTH: 19
<212> TYPE: RNA
<213> ORGANISM: Artificial sequence
<220> FEATURE:
<223> OTHER INFORMATION: Description of the artificial sequence:
      oligonucleotide

<400> SEQUENCE: 10
uuguagucug uauuucuug                                                      19

<210> SEQ ID NO 11
<211> LENGTH: 19
<212> TYPE: RNA
<213> ORGANISM: Artificial sequence
<220> FEATURE:
<223> OTHER INFORMATION: Description of the artificial sequence:
      oligonucleotide

<400> SEQUENCE: 11
agacuacaac aggcccaaa                                                      19

<210> SEQ ID NO 12
<211> LENGTH: 19
<212> TYPE: RNA
<213> ORGANISM: Artificial sequence
```

```
<220> FEATURE:
<223> OTHER INFORMATION: Description of the artificial sequence:
      oligonucleotide

<400> SEQUENCE: 12
uuugggccug uuguagucu                                                     19

<210> SEQ ID NO 13
<211> LENGTH: 19
<212> TYPE: RNA
<213> ORGANISM: Artificial sequence
<220> FEATURE:
<223> OTHER INFORMATION: Description of the artificial sequence:
      oligonucleotide

<400> SEQUENCE: 13
gucagauaca acagcauuu                                                     19

<210> SEQ ID NO 14
<211> LENGTH: 19
<212> TYPE: RNA
<213> ORGANISM: Artificial sequence
<220> FEATURE:
<223> OTHER INFORMATION: Description of the artificial sequence:
      oligonucleotide

<400> SEQUENCE: 14
aaaugcuguu guaucugac                                                     19

<210> SEQ ID NO 15
<211> LENGTH: 19
<212> TYPE: RNA
<213> ORGANISM: Artificial sequence
<220> FEATURE:
<223> OTHER INFORMATION: Description of the artificial sequence:
      oligonucleotide

<400> SEQUENCE: 15
gauagauagu ccacugaau                                                     19

<210> SEQ ID NO 16
<211> LENGTH: 19
<212> TYPE: RNA
<213> ORGANISM: Artificial sequence
<220> FEATURE:
<223> OTHER INFORMATION: Description of the artificial sequence:
      oligonucleotide

<400> SEQUENCE: 16
auucagugga cuaucuauc                                                     19

<210> SEQ ID NO 17
<211> LENGTH: 19
<212> TYPE: RNA
<213> ORGANISM: Artificial sequence
<220> FEATURE:
<223> OTHER INFORMATION: Description of the artificial sequence:
      oligonucleotide

<400> SEQUENCE: 17
ggauacggau augaaaucu                                                     19

<210> SEQ ID NO 18
<211> LENGTH: 19
<212> TYPE: RNA
<213> ORGANISM: Artificial sequence
<220> FEATURE:
```

```
<223> OTHER INFORMATION: Description of the artificial sequence:
      oligonucleotide

<400> SEQUENCE: 18
agauuucaua uccguaucc                                                      19

<210> SEQ ID NO 19
<211> LENGTH: 19
<212> TYPE: RNA
<213> ORGANISM: Artificial sequence
<220> FEATURE:
<223> OTHER INFORMATION: Description of the artificial sequence:
      oligonucleotide

<400> SEQUENCE: 19
guacgcaaac acuuuaugu                                                      19

<210> SEQ ID NO 20
<211> LENGTH: 19
<212> TYPE: RNA
<213> ORGANISM: Artificial sequence
<220> FEATURE:
<223> OTHER INFORMATION: Description of the artificial sequence:
      oligonucleotide

<400> SEQUENCE: 20
acauaaagug uuugcguac                                                      19

<210> SEQ ID NO 21
<211> LENGTH: 19
<212> TYPE: RNA
<213> ORGANISM: Artificial sequence
<220> FEATURE:
<223> OTHER INFORMATION: Description of the artificial sequence:
      oligonucleotide

<400> SEQUENCE: 21
aaugcaacuc ucaccuuaa                                                      19

<210> SEQ ID NO 22
<211> LENGTH: 19
<212> TYPE: RNA
<213> ORGANISM: Artificial sequence
<220> FEATURE:
<223> OTHER INFORMATION: Description of the artificial sequence:
      oligonucleotide

<400> SEQUENCE: 22
uuaaggugag aguugcauu                                                      19

<210> SEQ ID NO 23
<211> LENGTH: 19
<212> TYPE: RNA
<213> ORGANISM: Artificial sequence
<220> FEATURE:
<223> OTHER INFORMATION: Description of the artificial sequence:
      oligonucleotide

<400> SEQUENCE: 23
gaccaucaau aauuacacu                                                      19

<210> SEQ ID NO 24
<211> LENGTH: 19
<212> TYPE: RNA
<213> ORGANISM: Artificial sequence
<220> FEATURE:
<223> OTHER INFORMATION: Description of the artificial sequence:
``` oligonucleotide

<400> SEQUENCE: 24
aguguaauua uugaugguc                                                        19

<210> SEQ ID NO 25
<211> LENGTH: 19
<212> TYPE: RNA
<213> ORGANISM: Artificial sequence
<220> FEATURE:
<223> OTHER INFORMATION: Description of the artificial sequence:
      oligonucleotide

<400> SEQUENCE: 25
acguguaaag cugugacau                                                        19

<210> SEQ ID NO 26
<211> LENGTH: 19
<212> TYPE: RNA
<213> ORGANISM: Artificial sequence
<220> FEATURE:
<223> OTHER INFORMATION: Description of the artificial sequence:
      oligonucleotide

<400> SEQUENCE: 26
augucacagc uuuacacgu                                                        19

<210> SEQ ID NO 27
<211> LENGTH: 21
<212> TYPE: RNA
<213> ORGANISM: Artificial sequence
<220> FEATURE:
<223> OTHER INFORMATION: Description of the artificial sequence:
      oligonucleotide

<400> SEQUENCE: 27
uuaaagagag uggagccugg u                                                     21

<210> SEQ ID NO 28
<211> LENGTH: 21
<212> TYPE: RNA
<213> ORGANISM: Artificial sequence
<220> FEATURE:
<223> OTHER INFORMATION: Description of the artificial sequence:
      oligonucleotide

<400> SEQUENCE: 28
accaggcucc acucucuuua a                                                     21

<210> SEQ ID NO 29
<211> LENGTH: 19
<212> TYPE: RNA
<213> ORGANISM: Artificial sequence
<220> FEATURE:
<223> OTHER INFORMATION: Description of the artificial sequence:
      oligonucleotide

<400> SEQUENCE: 29
ggaggauacg gauaugaaa                                                        19

<210> SEQ ID NO 30
<211> LENGTH: 19
<212> TYPE: RNA
<213> ORGANISM: Artificial sequence
<220> FEATURE:
<223> OTHER INFORMATION: Description of the artificial sequence:
      oligonucleotide

```
<400> SEQUENCE: 30
uuucauaucc guauccucc                                              19

<210> SEQ ID NO 31
<211> LENGTH: 19
<212> TYPE: RNA
<213> ORGANISM: Artificial sequence
<220> FEATURE:
<223> OTHER INFORMATION: Description of the artificial sequence:
      oligonucleotide

<400> SEQUENCE: 31
gagcuaaauu acacauuga                                              19

<210> SEQ ID NO 32
<211> LENGTH: 19
<212> TYPE: RNA
<213> ORGANISM: Artificial sequence
<220> FEATURE:
<223> OTHER INFORMATION: Description of the artificial sequence:
      oligonucleotide

<400> SEQUENCE: 32
ucaaugugua auuuagcuc                                              19

<210> SEQ ID NO 33
<211> LENGTH: 19
<212> TYPE: RNA
<213> ORGANISM: Artificial sequence
<220> FEATURE:
<223> OTHER INFORMATION: Description of the artificial sequence:
      oligonucleotide

<400> SEQUENCE: 33
caucuacgcu gacaaugaa                                              19

<210> SEQ ID NO 34
<211> LENGTH: 19
<212> TYPE: RNA
<213> ORGANISM: Artificial sequence
<220> FEATURE:
<223> OTHER INFORMATION: Description of the artificial sequence:
      oligonucleotide

<400> SEQUENCE: 34
uucauuguca gcguagaug                                              19

<210> SEQ ID NO 35
<211> LENGTH: 19
<212> TYPE: RNA
<213> ORGANISM: Artificial sequence
<220> FEATURE:
<223> OTHER INFORMATION: Description of the artificial sequence:
      oligonucleotide

<400> SEQUENCE: 35
cucuauauuu agauuguua                                              19

<210> SEQ ID NO 36
<211> LENGTH: 19
<212> TYPE: RNA
<213> ORGANISM: Artificial sequence
<220> FEATURE:
<223> OTHER INFORMATION: Description of the artificial sequence:
      oligonucleotide
```

<400> SEQUENCE: 36
uaacaaucua aauauagag 19

<210> SEQ ID NO 37
<211> LENGTH: 19
<212> TYPE: RNA
<213> ORGANISM: Artificial sequence
<220> FEATURE:
<223> OTHER INFORMATION: Description of the artificial sequence:
oligonucleotide
<400> SEQUENCE: 37
gguugaaugc accacucaa 19

<210> SEQ ID NO 38
<211> LENGTH: 19
<212> TYPE: RNA
<213> ORGANISM: Artificial sequence
<220> FEATURE:
<223> OTHER INFORMATION: Description of the artificial sequence:
oligonucleotide
<400> SEQUENCE: 38
uugaguggug cauucaacc 19

<210> SEQ ID NO 39
<211> LENGTH: 19
<212> TYPE: RNA
<213> ORGANISM: Artificial sequence
<220> FEATURE:
<223> OTHER INFORMATION: Description of the artificial sequence:
oligonucleotide
<400> SEQUENCE: 39
ugguagaauu ggagaguaa 19

<210> SEQ ID NO 40
<211> LENGTH: 19
<212> TYPE: RNA
<213> ORGANISM: Artificial sequence
<220> FEATURE:
<223> OTHER INFORMATION: Description of the artificial sequence:
oligonucleotide
<400> SEQUENCE: 40
uuacucucca auucuacca 19

<210> SEQ ID NO 41
<211> LENGTH: 19
<212> TYPE: RNA
<213> ORGANISM: Artificial sequence
<220> FEATURE:
<223> OTHER INFORMATION: Description of the artificial sequence:
oligonucleotide
<400> SEQUENCE: 41
cagugugguu uguguuuga 19

<210> SEQ ID NO 42
<211> LENGTH: 19
<212> TYPE: RNA
```
<213> ORGANISM: Artificial sequence
<220> FEATURE:
<223> OTHER INFORMATION: Description of the artificial sequence:
      oligonucleotide

<400> SEQUENCE: 42
ucaaacacaa accacacug                                                19

<210> SEQ ID NO 43
<211> LENGTH: 19
<212> TYPE: RNA
<213> ORGANISM: Artificial sequence
<220> FEATURE:
<223> OTHER INFORMATION: Description of the artificial sequence:
      oligonucleotide

<400> SEQUENCE: 43
cggaagcuau gacuuauga                                                19

<210> SEQ ID NO 44
<211> LENGTH: 19
<212> TYPE: RNA
<213> ORGANISM: Artificial sequence
<220> FEATURE:
<223> OTHER INFORMATION: Description of the artificial sequence:
      oligonucleotide

<400> SEQUENCE: 44
ucauaaguca uagcuuccg                                                19

<210> SEQ ID NO 45
<211> LENGTH: 19
<212> TYPE: RNA
<213> ORGANISM: Artificial sequence
<220> FEATURE:
<223> OTHER INFORMATION: Description of the artificial sequence:
      oligonucleotide

<400> SEQUENCE: 45
uucuccgaac gugucacgu                                                19

<210> SEQ ID NO 46
<211> LENGTH: 19
<212> TYPE: RNA
<213> ORGANISM: Artificial sequence
<220> FEATURE:
<223> OTHER INFORMATION: Description of the artificial sequence:
      oligonucleotide

<400> SEQUENCE: 46
acgugacacg uucggagaa                                                19
```